US007388087B2

(12) United States Patent  
Zuckermann (10) Patent No.: US 7,388,087 B2  
(45) Date of Patent: Jun. 17, 2008

(54) ENHANCEMENT OF IMMUNE RESPONSE TO VACCINE BY INTERFERON ALPHA

(75) Inventor: Federico A. Zuckermann, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 448 days.

(21) Appl. No.: 10/416,315

(22) PCT Filed: Nov. 9, 2001

(86) PCT No.: PCT/US01/50189

§ 371 (c)(1),  
(2), (4) Date: Oct. 3, 2003

(87) PCT Pub. No.: WO02/060921

PCT Pub. Date: Aug. 8, 2002

(65) Prior Publication Data

US 2004/0101513 A1  May 27, 2004

Related U.S. Application Data

(60) Provisional application No. 60/247,289, filed on Nov. 9, 2000.

(51) Int. Cl.  
C07H 21/04 (2006.01)
(52) U.S. Cl. ............... 536/23.52; 536/23.5; 536/23.1
(58) Field of Classification Search ........... 536/23.52, 536/23.5, 23.1  
See application file for complete search history.

(56) References Cited

U.S. PATENT DOCUMENTS

| | | |
|---|---|---|
| 4,124,702 A | 11/1978 | Lampson |
| 4,389,395 A | 6/1983 | Lerner |
| 4,820,514 A | 4/1989 | Cummins |
| 5,582,824 A | 12/1996 | Goeddel |
| 5,593,667 A | 1/1997 | Kung |
| 5,594,107 A | 1/1997 | Potter |
| 5,730,971 A | 3/1998 | Ishiwata |
| 5,827,694 A | 10/1998 | Capon |
| 5,831,023 A | 11/1998 | Capon |
| 5,976,539 A | 11/1999 | Scott |
| 5,989,563 A | 11/1999 | Chladek |
| 6,042,830 A | 3/2000 | Chladek |
| 6,251,397 B1 | 6/2001 | Paul |

FOREIGN PATENT DOCUMENTS

| | | | |
|---|---|---|---|
| EP | 0 803 573 A1 | * | 10/1997 |
| WO | WO 98/08947 | | 3/1998 |
| WO | WO 98/08947 | * | 5/1998 |

OTHER PUBLICATIONS

Dufour et al. (Oct. 2000) J. Interfer. & Cyt. Res., vol. 20, 889-895.*
Somasundaram et al. (1999) Vet. Immunol. & Immunopath., vol. 70, 277-287.*
Tuting et al. (Apr. 1999) Gene Therapy, vol. 6, 629-636.*
Albina, E. et al., "Interferon-$\alpha$ response to swine arterivirus (PoAV), the porcine reproductive and respiratory syndrome virus," J. Interferon and Cytokine Research 18:485-490, 1998.
Arnon, R. (Ed.), *Synthetic Vaccines*, CRC Press, Inc., Boca Raton, FL 1:83-92, 1987.
Buddaert, W. et al., "In vivo and in vitro interferon (IFN) studies with the porcine reproductive and respiratory syndrome virus (PRRSV)," Adv. Exp. Med. Biol. 440:461-467, 1998.
Cousens, L. P. et al., "Two roads diverged: Interferon $\alpha/\beta$- and interleukin 12-mediated pathways in promoting T cell interferon $\gamma$ responses during viral infection," J. Exp. Med. 189(8):1315-1327, 1999.
Horner, A. A. et al., "Immunostimulatory DNA is a potent mucosal adjuvant," Cellular Immunology 190:77-82, 1998.
Lachman, L. B. et al., "Cytokine-containing liposomes as adjuvants for subunit vaccines," Chapter 29 in *Vaccine Design: The Subunit and Adjuvant Approach*, M.F. Powell and M. J. Newman (eds.), Plenum Press, New York, pp. 659-671.
Lachman, L.B. et al., "Cytokine-containing liposomes as vaccine adjuvants," Abstract only, Eur. Cytokine Netw. 7(4):693-698, 1996.
Levy, H. B. et al., "A modified polyriboinosinic-polyribocytidylic acid complex that induces interferon in primates," J. Infectious Diseases 132(4):434-439, 1975.
Loewen, K. G. et al., "Interferon induction in piglets with polyinosinic:polycytidylic acid complexed with poly-L-lysine and carboxymethylcellulose," Res. Vet. Sci. 44:132-133, 1988.
Mardassi, H. et al., "Identification of major differences in the nucleocapsid protein genes of a Quebec strain and European strains of porcine reproductive and respiratory syndrome virus," J. Gen. Virol. 75:681-685, 1994.
Osorio, F. A. et al., "PRRSV: Comparison of commercial vaccines in their ability to induce protection against current PRRSV strains of high virulence," Allen D. Leman Swine Conference, pp. 176-182, 1998.
Pachuk, C.J. et al., "DNA vaccines—challenges in delivery," Abstract only, Curr. Opin. Mol. Ther. 2(2):188-198, 2000.
Roman, M. et al., "Immunostimulatory DNA sequences function as T helper-1-promoting adjuvants," Nature Medicine 3(6):849-854, 1997.

(Continued)

*Primary Examiner*—Anne M. Wehbe  
(74) *Attorney, Agent, or Firm*—Greenlee, Winner, and Sullivan, P.C.

(57) ABSTRACT

Exogenous cDNA capable of expressing interferon $\alpha$ activity, exogenous interferon $\alpha$ protein, inducers of endogenous interferon $\alpha$ protein activity, inducers of endogenous interferon $\beta$ protein activity, inducers of endogenous interfereon $\Gamma$ activity, or inducers of other immune-enhancing activity can be combined with a vaccine to enhance an immune response. Specifically disclosed are adjuvant and vaccine combinations where the adjuvant comprises a cDNA capable of expressing interferon $\alpha$ activity, a complex comprising polyriboinosinic-polyribocytidilic acid, or a complex comprising polyriboinosinic-polyribocytidilic acid, poly-L-lysine, and carboxymethylcellulose and where the vaccine is a live vaccine virus derived from a virus causing porcine reproductive and respiratory syndrome disease.

**

OTHER PUBLICATIONS

Sprent, J. et al., "T-cell proliferation in vivo and the role of cytokines," Phil. Trans. R. Soc. Lond. B 355:317-322, 2000.

Thanawongnuwech, R. et al., "Effect of porcine reproductive and respiratory syndrome virus (PRRSV) (isolate ATCC VR-2385) infection on bactericidal activity of porcine pulmonary intravascular macrophages (PIMs): in vitro comparisons with pulmonary alveolar macrophages (PAMs)," Vet. Immunol. Immunopathol. 59:323-335, 1997.

Van Reeth, K. et al., "Differential production of proinflammatory cytokines in the pig lung during different respiratory virus infections: correlations with pathogenicity," Research in Veterinary Science 67:47-52, 1999.

Van Reeth, K., "Cytokines in the pathogenesis of influenza," Veterinary Microbiology 74:109-116, 2000.

Van Slooten, M. L. et al., "Liposomes as sustained release system for human interferon-γ: biopharmaceutical aspects," Biochimica et Biophysica Acta 1530:134-145, 2001.

Van Slooten, M. L. et al., "Liposomes containing interferon-gamma as adjuvant in tumor cell vaccines," Pharm. Res. 17(1):42-48, 2000.

Vogel, F.R. et al., "A compendium of vaccine adjuvants and excipients," Chapter 7 in: *Vaccine Design: The Subunit and Adjuvant Approach*, M. F. Powell and M. J. Newman (eds.), Plenum Press, New York, pp. 141-227, 1995.

Wensvoort, G. et al., "Antigenic comparison of Lelystad virus and swine infertility and respiratory syndrome (SIRS) virus," J. Vet. Diagn. Invest. 4:134-138, 1992.

Zuckermann, F. A. et al., "Interleukin-12 enhances the virus-specific interferon gamma response of pigs to an inactivated pseudorabies virus vaccine," Vet. Immunol. Immunopath. 63:57-67, 1998.

Lachman, L. B. et al., "Cytokine-containing liposomes as adjuvants for subunit vaccines," Chapter 29 in *Vaccine Design: The Subunit and Adjuvant Approach*, M.F. Powell and M. J. Newman (eds.), Plenum Press, New York, pp. 659-971, 1995.

R. Dijkmans et al., Sequence of the porcine interferon-gamma (IFN-gamma) gene, Nucleic Acids Research 18(14):4259, 1990.

J. J. Kim et al., Coimmunization with IFN-gamma or IL-2, but not IL-13 or IL-4 cDNA can enhance Th1-type DNA vaccine-induced immune responses in vivo, J Interferon and Cytokine Research 20:311-319, 2000.

D. Mege et al., The porcine family of interferon-w [omega]: Cloning, structural analysis, and functional studies of five related genes, J. Interferon Research 11:341-350, 1991.

International Search Report, International Application No. PCT/US01/50189, Apr. 28, 2003, 4 pages.

International Preliminary Examination Report, International Application No. PCT/US01/50189, Jan. 5, 2004, 5 pages.

\* cited by examiner

```
Top lines   = SEQ ID NO:4
Bottom lines = SEQ ID NO:3

M   A   P   T   S   A   F   L   T   A   L   V      12
TCTGCAAGGTTCCCAATGGCCCCAACCTCAGCCTTCCTCACGGCCCTGGT          50

L   L   S   C   N   A   I   C   S   L   G   C   D   L   P   Q   T   29
GCTACTCAGCTGCAATGCCATCTGCTCTCTGGGCTGTGACCTGCCTCAGA         100

H   S   L   A   H   T   R   A   L   R   L   L   A   Q   M   R   45
CCCACAGCCTGGCTCACACCAGGGCCCTGAGGCTCCTGGCACAAATGAGG         150

R   I   S   P   F   S   C   L   D   H   R   R   D   F   G   S   P   62
AGAATCTCTCCCTTCTCCTGCCTGGACCACAGAAGGGACTTTGGATCCCC         200

H   E   A   F   G   G   N   Q   V   Q   K   A   Q   A   M   A   L    79
TCATGAGGCTTTTGGGGGCAACCAGGTCCAGAAGGCTCAAGCCATGGCTC         250

V   H   E   M   L   Q   Q   T   F   Q   L   F   S   T   E   G      95
TGGTGCATGAGATGCTCCAGCAGACCTTCCAGCTCTTCAGCACAGAGGGC         300

S   A   A   A   W   N   E   S   L   L   H   Q   F   C   T   G   L   112
TCGGCTGCTGCCTGGAATGAGAGCCTCCTGCACCAGTTCTGCACTGGACT   350

D   Q   Q   L   R   D   L   E   A   C   V   M   Q   E   A   G   L   129
GGATCAGCAGCTCAGGGACCTGGAAGCCTGTGTCATGCAGGAGGCGGGGC         400

E   G   T   P   L   L   E   E   D   S   I   L   A   V   R   K      145
TGGAAGGGACCCCCCTGCTGGAGGAGGACTCCATCCTGGCTGTGAGGAAA         450

Y   F   H   R   L   T   L   Y   L   Q   E   K   S   Y   S   P   C   162
TACTTCCACAGACTCACCCTCTATCTGCAAGAGAAGAGCTACAGCCCCTG         500

A   W   E   I   V   R   A   E   V   M   R   S   F   S   S   S   R   179
TGCCTGGGAGATCGTCAGGGCAGAAGTCATGAGATCCTTCTCTTCCTCCA         550

N   L   Q   D   R   L   R   K   K   E   *             190
GAAACCTGCAAGACAGACTCAGGAAGAAGGAGTGACAGAC         590
```

ENHANCEMENT OF IMMUNE RESPONSE TO VACCINE BY INTERFERON ALPHA

CROSS-REFERENCE TO RELATED APPLICATIONS

This application is the National Stage of International Application No. PCT/US01/50189, filed Nov. 9, 2001, which claims the benefit under 35 U.S.C. §119(e) of U.S. Provisional Application No. 60/247,289, filed Nov. 9, 2000.

FIELD OF THE INVENTION

This invention relates to vaccine enhancement particularly for use in pigs and more particularly for porcine reproductive and respiratory syndrome (PRRS).

BACKGROUND OF THE INVENTION

There have been considerable efforts to identify substances that potentiate an immune response to a vaccine. For example, the cytokine interleukin-12 (IL-12) was reported to be useful as an adjuvant in U.S. Pat. No. 5,976,539, where the IL-12 was provided as a protein or nucleotide coding sequence. Interferon alpha is another cytokine reported to be useful as an oral vaccine adjuvant in, e.g., U.S. Pat. No. 4,820,514. In this patent only the protein form of the cytokine was used. Furthermore, oral administration of the protein resulted in a systemic effect, and too low or too high a dose of the protein was undesirable. It would be advantageous to generate a local adjuvant effect that does not require oral route administration of the protein and is not so dependent upon dose level.

An important aspect of the development of an adjuvant is the two-fold breadth potential for its application. Such breadth concerns both the underlying immune system and the target of the immune system's defense. An adjuvant can be useful in many mammalian species, if the adjuvant has the capacity to influence common attributes of the immune systems of those species. Further, if the targets of the immune system analogously have common attributes in how they are susceptible to immune responses, then an adjuvant stimulating an immune response should have broad applicability in defending against a variety of targets.

A need is recognized in the art for enhanced veterinary vaccines. An area of significant need for enhanced vaccines is manifested by outbreaks of porcine reproductive and respiratory syndrome (PRRS). PRRS has a severe impact on the health and reproductive ability of swine. To address this problem, vaccines were developed for the etiological agent of PRRS as reported in U.S. Pat. Nos. 5,989,563 and 6,042,830. In these patents, a viral agent capable of causing PRRS disease was isolated and used to develop a modified-live virus (MLV) vaccine. Classically, modified-live virus vaccines are derived from virulent strains that are modified by techniques such as growth in vitro, with or without alteration of conventional in vitro conditions, passage in non-natural host cells, or a combination of those techniques. In the U.S. Pat. Nos. 5,989,563 and 6,042,830 patents, the reported parental virulent porcine viral isolate is ATCC-VR2332. From this isolate, a modified vaccine virus was generated by attenuation through multiple passages of growth in vitro in simian cell culture. Thus ATCC-VR2495 was reported to be a suitable MLV for use in vaccine formulations for commercial purposes.

Currently the PRRS vaccines, even those that are of the MLV type, do not confer adequate protection from disease. In a study designed to test the efficacy of PRRS vaccines, currently available products failed to completely protect pigs from clinical disease caused by certain virulent strains of PRRS virus. Osorio et al., 1998. It was speculated that deficiencies in the pig's ability to mount cellular immune responses to PRRS virus may promote the evolution of more virulent strains in addition to predisposing the animal to virus infection. Alternatively, it was suggested that the PRRS virus itself may be responsible for altering the cellular immune response. Osorio et al., 1998.

Although the mechanisms that mediate protective immunity against PRRS virus are unknown, attempts have been made to study the characteristics of immunity induced by either infection with wild-type PRRS virus or vaccination with a commonly used PRRS modified live virus (MLV) vaccine. An example of PRRS MLV is described in U.S. Pat. Nos. 5,989,563 and 6,042,830. Exposure of an animal to either the wild-type virus or the MLV form of the PRRS virus does not stimulate a strong viral purging immunity. Virus-specific T cells secreting interferon gamma and virus neutralizing antibodies, both of which have the potential to mediate viral purging, are detected only several weeks after exposure of pigs to PRRS virus. One possible explanation for the failure of PRRS virus to stimulate the development of a strong viral purging immunity is that PRRS virus, in contrast to other viruses, is a poor stimulator of interferon alpha (abbreviated IFNalpha or IFN$\alpha$) production in swine. Albina et al., 1998. Buddaert et al., 1998. Van Reeth et al., 1999. Consistent with this explanation is a reference indicating that IFN$\alpha$ can affect the development of anti-viral T cell interferon gamma (IFN-gamma or IFN$\gamma$) responses and peak anti-viral immune defenses. Cousens et al., 1999.

There is considerable evidence in the art, however, that mere augmentation of IFN$\alpha$ in conjunction with wild-type PRRS virus infection or PRRS MLV exposure would be expected to have no significant positive effect on an immune response. For example, while the importance of IFN$\alpha$ on IFN$\gamma$ response was shown in the mouse, it is unknown whether a similar response would occur in the pig. If the level of IFN$\alpha$ in the pig is indeed unnecessary for the induction of an adequate IFN$\gamma$ response, then additional IFN$\alpha$ present in the pig would have no effect on immune response. Furthermore, while it is believed that PRRS virus can avoid the effects of the interferon system by blocking the production of IFN or by inhibiting its effects, it is not known which method of avoidance, blocking production or inhibition of effects, is significant or whether both methods function in a given organism. Albina, 1998. The lack of understanding about how PRRS directly or indirectly affects the innate IFN$\alpha$ response also makes it unclear that any attempts to further induce endogenous IFN$\alpha$, to add IFN$\alpha$ (exogenous), or to add IFN$\alpha$ cDNA to express IFN$\alpha$ would enhance the immune response to PRRS. For example, if PRRS alters an IFN$\alpha$ response by inhibition of IFN$\alpha$ expressed protein, then it would be expected that no attempt to boost the level of IFN$\alpha$ would succeed in enhancing the immune response to PRRS. In fact, until now it has appeared unlikely that boosting the level of IFN$\alpha$ in combination with PRRS MLV exposure would have any clear effect on enhanced immunity. The present invention makes the unexpected discovery that boosting the level of IFN$\alpha$ in an animal can indeed yield enhanced immunity.

The fact that IFN$\alpha$ can enhance immunity coupled with any live virus vaccine is particularly surprising in light of the normal function of IFN$\alpha$. Since IFN$\alpha$ is known to have a negative effect on the process of viral replication, one might reasonably expect that an immune response from exposure to a live vaccine virus would be negatively affected by a boosted level of IFNα.

Even more strikingly, evidence indicates that a heightened level of IFNα could in fact contribute to a disease state in an infected or exposed animal. For example, the proinflammatory cytokines IFNα, tumor necrosis factor alpha, and interleukin-1 have been shown to play key roles in several respiratory disease conditions. Van Reeth, 2000. From studies involving various porcine virus infections, it was proposed that the relatively low IFNα response following PRRS infection is related to the lack of acute respiratory disease, severe lung necrosis, and inflammation. Van Reeth, 1999. According to Van Reeth, the absence of a particular 'cytokine combination' such as IFNα, TNFa, and IL-1 during PRRS infection may in part explain the mild respiratory pathology and the absence of respiratory disease. As a corollary to this proposal, the augmentation of IFNα exogenously or endogenously, is predicted to contribute to a more severe disease state rather than to enhance immunity.

Prior research also reveals that at least three other cytokines, IFNγ, IL-12, and IL-18, share the capacity of type one interferons (including IFNalpha and IFNbeta) to augment immunity by inducing strong T cell proliferation under in vivo conditions. Sprent et al., 2000. Given that "the mechanisms involved here are still unknown," it is unexpected that a single cytokine such as IFNα serves to enhance an in vivo immune response, if there are multiple independent pathways for achieving a similar result. Currently, "the biological significance" of at least one type of immune enhancement, T-cell proliferation, "induced by type 1 interferons and other cytokines in vivo is still unclear." Sprent et al., 2000.

Non-human animal interferons are described in both protein form, U.S. Pat. No. 5,831,023, and in cDNA form (cDNA that expresses IFNα), U.S. Pat. No. 5,827,694. While these references disclose potential use of IFNα protein, including IFNα expressed from cDNA, in pharmaceutical compositions for prophylactic or therapeutic treatment of non-human animals, the particular use of IFNα in combination with a live virus vaccine is not disclosed and would be disfavored by those skilled in the art for the reasons discussed herein.

Substances capable of inducing endogenous interferon have been identified. Levine, 1970. These substances include live viruses with either DNA or RNA genomes, double stranded RNA, DNA from protozoan parasites, bacterial endotoxin, mannan, mitogens (phytohemagglutinin, streptolysin O, and poke-week mitogen), statolon, helenine, and synthetic polyribonucleotides.

Other inducers of interferon have been identified. In U.S. Pat. No. 5,730,971, the substances flavin adenine dinucleotide, flavin adenine mononucleotide, and riboflavin (vitamin B2) are disclosed as potential contributors to the potentiation of an interferon response.

More recently, an adjuvant role for certain short bacterial immunostimulatory DNA sequences was proposed due to their ability to stimulate T helper-1 responses in animals vaccinated with genetic versions of antigens. Roman M et al., 1997, Nature Med 3:849. These DNA sequences are known to contain CpG (Cytosine-Guanine) motifs that are believed to be significant in the immunostimulatory capacity. However, such sequences are suggested for use in vaccine compositions where the vaccine component or subunit thereof is inactivated and not for use with live organisms such as viruses or modified live viruses.

Inducers of interferon were reported as having potential for resisting viral infection and for treating viral diseases as disclosed in U.S. Pat. Nos. 4,124,702 and 4,389,395. In U.S. Pat. No. 4,124,702, complexes of polymers are reported for induction of interferon production. The polymers can be synthetic homopolynucleotides such as polyriboinosinic acid and polyribocytidylic acid mixed in a 1:1 molar ratio (polyIC). For example, a modified polyIC complex was reported to induce serum interferon in primates in a fashion superior to polyIC. Levy, 1975. In U.S. Pat. No. 4,389,395, complexes comprising polyIC, poly-L-lysine and carboxymethylcellulose are reported for use in the induction of endogenous interferon; these complexes are referred to as polyICLC. Both polyIC and polyICLC were assessed for their ability to induce interferon responses in pigs. Loewen, 1986; Loewen, 1988. Jordan, 1995. It is believed that the polyIC and polyICLC provide preferential enhancement of cell-mediated versus humoral immunity. Alternatively, the benefits of polyIC and polyICLC is believed to be the result of quantitative improvement, for example in increases of the numbers of activated cells or the amount of antibody produced. These and other possible non-exclusive mechanisms are ways that interferon inducers can aid in immunity.

The present invention provides methods and compositions that enhance the efficacy of vaccines, particularly modified live viruses (MLV). In particular, the invention enhances the immunity in pigs compared with the immunity achieved by vaccination with PRRS MLV alone. The ability to enhance immunity is shown by combining a vaccine with any of three adjuvants: IFNα protein, IFNα cDNA, and inducers of endogenous IFNα production.

SUMMARY OF THE INVENTION

The invention comprises compositions and methods for enhancing the immune response of an animal to a viral vaccine. The inventive method comprises administration of a therapeutic composition that enhances the level of one or more interferons, particularly interferon alpha, in an animal that is being treated with the viral vaccine. The level of interferon in the treated animal is enhanced, at least locally in certain tissues or cells, over levels of the interferon in the untreated animal to enhance the immune response of the animal to a viral vaccine. The therapeutic composition that enhances interferon level preferably comprises a nucleic acid from which an interferon functional in an animal can be expressed in cells or tissue of the animal, a material that can induce or enhance interferon expression in cells or tissue of the animal, or both in a pharmaceutically acceptable carrier. This therapeutic composition acts as an adjuvant for enhancing the immune response of the animal to a viral vaccine. The viral vaccine and the therapeutic composition of this invention are preferably contemporaneously administered to the animal. The therapeutic composition of this invention can also comprise one or more known adjuvants other than interferon for enhancing immune responses.

In one embodiment, the amount of expressible nucleic acid encoding an interferon in the therapeutic composition is sufficient to facilitate expression of encoded interferon in animal cells or tissue and preferably is present in the composition in an amount sufficient to express encoded interferon in animal cells or tissue at a level that causes an enhancement of immune response of the animal to a viral vaccine. The amount of a material that induces or enhances interferon expression present in the composition is sufficient to induce or enhance expression of endogenous interferon or to induce or enhance expression of exogenously administered expressible nucleic acid encoding interferon in cells or tissue of the animal.

The invention provides methods and compositions for enhancing the immunity of an animal to a virus, particularly a modified live virus by administering to the animal a vaccine for the virus, and administering to the animal a therapeutic composition of this invention comprising an interferon and/or an interferon inducer compound in an amount or combined amount sufficient to enhance the immunity of the animal to the virus provided by administration of the vaccine alone. In one aspect of this method, an enhanced immune response is assessed by stimulation of IFNgamma.

The invention also provides methods and compositions for conferring protective immunity against clinical disease. In a specific embodiment, the methods and compositions of the invention confer partial or complete protection against PRRS.

In one embodiment, the vaccine and the immunity enhancing interferon and/or interferon inducer compound are administered subcutaneously at the same time (i.e., within about 1 hour to several hours of each other.)

The therapeutic compositions and methods of this invention are applicable for any viral vaccine, for any species of animal, for any homologous source of nucleic acid encoding interferon, including interferon alpha or beta that is functional in the given species of animal, and for any material that induces or enhances expression of an interferon in the animal. In some cases, heterologous sources of nucleic acid can suffice as a substitute for a homologous source. As a nonexclusive heterologous example, a murine source of a nucleic acid encoding IFNα or other interferon can be used in conjunction with any live virus vaccine, or more specifically a PRRS MLV vaccine, for administration to a porcine species. As another nonexclusive example, a porcine source of IFNα or nucleic acid encoding another interferon coding nucleic acid sequence can be used in conjunction with any live virus vaccine where the vaccine and porcine coding sequence for IFNα or other interferon are administered to a heterologous animal species, e.g., any ungulate.

The therapeutic compositions and methods of this invention are applicable for arteriviridae and other related viruses. Examples of such viruses include, but are not limited to, equine arteritis virus, simian hemorrhagic fever virus, and PRRS virus.

Nucleic acids encoding the interferon, e.g., alpha and beta, can be natural or synthetic. The natural or synthetic nucleic acids can be truncations of natural forms or derivatives of natural forms containing base changes that encode protein variants (or truncations) with conservative amino acid changes compared to a natural form of a given species or type of interferon. Any useful nucleic acid truncations or derivatives encode a protein or polypeptide that substantially retains the activity of a given species or type of interferon. Nucleic acids encoding an interferon are expressible in cells or tissue of an animal to which the expressible nucleic acids are delivered. Expressible nucleic acid sequences are under the regulatory control of regulatory elements including a promoter, polyadenylation signal sequence and optionally other related sequences that control expression or expression levels of the nucleic acid sequence in a cell or tissue of a given animal. The promoter employed may be constitutive or may be direct selective expression in a selected tissue or in a selected environment. An expressible nucleic acid, as used herein, comprises any nucleic acid sequences necessary for expression of the interferon coding sequence operably linked to that coding sequence for expression in a cell or tissue of an animal. The expressible nucleic acid encoding an interferon can be provided in an expression vector, such as a plasmid, which optionally contains other expressible coding sequences, such as selectable or detectible markers.

Regulatory sequences in the expressible nucleic acid can be heterologous or homologous to the nucleic acid encoding interferon, e.g., the expressible nucleic acid can contain a polyadenylation sequence of the natural interferon coding sequence or a polyadenylation sequence obtained from another source, i.e., from another gene. The regulatory sequences may be obtained from nucleic acid of the same species as the interferon coding sequences or from nucleic acid of a different species, e.g., a polyadenylation sequence from a bovine gene can be employed with an interferon coding sequence of a porcine animal.

In particular, the invention comprises compositions and methods for enhancing the immune response of porcine animals to a PRRS vaccine. The compositions and methods utilize the ability of exogenous interferon coding sequences, as administered in expressible nucleic acid, inducers of endogenous interferon activity, e.g., inducers of endogenous interferon alpha protein activity, inducers of endogenous interferon beta protein activity, and inducers of endogenous interferon gamma activity, or mixtures thereof, in combination with a vaccine composition to enhance an immune response.

In one embodiment, a therapeutic composition comprises an expressible nucleic acid sequence encoding an interferon alpha and a pharmaceutically acceptable carrier. The nucleic acid sequence is present in the composition in an amount sufficient to express an amount of interferon alpha sufficient to exhibit enhancement of immune reponse on delivery to an animal, particularly a pig. The composition can be provided with appropriate components to facilitate delivery and expression of the nucleic acid in a desired selected organism, such as a pig. The composition optionally combines expressible interferon-α nucleic acid sequence with a live virus vaccine, or more specifically a PRRS MLV vaccine. An exemplary interferon-α nucleic acid sequence is that of FIG. 1.

In another embodiment, a method is provided for enhancing immunity by administering a vaccine composition to an animal and administering an adjuvant composition comprising an expressible nucleic acid for interferon-α to an animal. The order of administration of the vaccine composition and the adjuvant composition is preferably contemporaneous, i.e., sufficiently close in time so that the adjuvant results in an enhancement of immune response in the animal. Administration of the two compositions can be simultaneous or sequential; if administration is sequential, either the adjuvant can be administered to the animal first and the vaccine second, or vice versa. Contemporaneous administration encompassed administration of the adjuvant up to about one week before or one week after administration of the vaccine. Preferably the vaccine and adjuvant are administered to the animal on the same day and more preferably within several hours of each other.

In another embodiment of the invention, the immunity enhancing interferon or interferon enhancer molecule is administered to the same localized site as the vaccine.

In a specific embodiment, a method is provided for enhancing immunity by first administering a vaccine composition to an animal and thereafter administering the adjuvant composition comprising an expressible nucleic acid encoding interferon alpha. The adjuvant composition is preferably administered up to one week after the vaccine is administered.

In another embodiment, a method for enhancing immunity by administering to an animal a vaccine composition and administering to an animal an adjuvant composition comprising a material capable of inducing an IFNα response, IFNβ response, IFNγ response, or other response resulting in enhanced antiviral immunity is provided. The interferon γ response can be induced by the activity of interferon α, interferon β, or other mediator. In a particular embodiment, the material that induces or enhances interferon activity is a pharmaceutically acceptable composition comprising polyriboinosinic-polyribocytidylic acid, poly-L-lysine and carboxymethylcellulose optionally in combination with a pharmaceutically acceptable carrier. In another particular embodiment, said material is a pharmaceutically acceptable composition comprising polyriboinosinic acid-polyribocytidylic acid complex optionally in combination with a pharmaceutically acceptable carrier. Alternatively, the material can be any of the following which induce an interferon response, particularly an interferon α response in a given animal: live RNA viruses, Inactivated RNA viruses, Live DNA viruses, Inactivated DNA viruses, DNA from DNA viruses, DNA from bacteria, DNA from bacterial plasmids, DNA from synthetic plasmids, DNA from organisms in the family Rickettsiae, DNA from protozoan parasites, Bacterial endotoxin, Double-stranded RNA, Double stranded synthetic polyribonucleotides; Phytohemagglutinin; Mannan; Streptolysin O, Poke-weed mitogen, Statolon, Helenine, Flavin adenine mononucleotide, Flavin adenine dinucleotide, and Riboflavin.

In yet another embodiment, the invention relates to an adjuvant composition comprising an expressible interferon α having the sequence of SEQ ID NO:3 present in the composition at a level such that the level of interferon α expressed in an animal to which the composition is administered is sufficient to enhance immune response to a vaccine administered to the animal. In a particular aspect of this embodiment the animal is a pig.

In yet another embodiment, the invention provides a method for enhancing an immune response of an animal to a vaccine comprising the steps of administering a vaccine antigen composition to an animal in an amount effective to stimulate an immune response and administering to the animal an adjuvant composition comprising nucleic acid having capability of expressing interferon activity in an amount effective to potentiate the immune response to the vaccine antigen composition. In one aspect of this method the interferon is a Type 1 interferon, interferon alpha or interferon beta. In another aspect of the method the interferon is porcine interferon alpha. In another aspect of the method the animal that is vaccinated is a pig. In yet another aspect of the method the vaccine antigen composition comprises a live vaccine virus. In some aspects of this method the live vaccine virus is derived from an agent capable of causing clinical signs of porcine reproductive and respiratory syndrome disease.

BRIEF DESCRIPTION OF THE DRAWINGS

FIG. 1: Nucleotide (SEQ ID NO:3) and predicted Amino Acid sequence (SEQ ID NO:4) of amplified porcine interferon-α cDNA. The nucleotides and amino acids that are divergent from those of sequence in GenBank:X57191 are in bold and underlined.

FIG. 2: Schematic representation of plasmid pINA3. The relative positions and direction of transcription of the cytomegalovirus promoter (CMV), porcine interferon alpha cDNA, bovine growth hormone polyadenylation signal sequence (BGH polyA), SV40 origin, bacterial neomycin resistance gene, SV40 polyadenylation signal sequence (SV40 polyA) and bacterial ampicillin resistance gene are indicated.

FIG. 3: Adjuvant effect of IFNalpha cDNA on IFN-gamma response to PRRS MLV in 8 week old pigs; see Example 2. Adjuvant effect of interferon-alpha on the virus-specific interferon-gamma response of swine to a PRRS modified live virus (MLV) vaccine. Groups of pigs (5 per group) were immunized with a commercial PRRS MLV vaccine either alone or with the simultaneous intramuscular injection of 200 μg of the plasmid pINA3 that contains the cDNA for porcine IFN-alpha. At the indicated times after immunization peripheral blood mononuclear cells were isolated from those animals and the number of PRRS virus-specific interferon-gamma secreting cells determined by ELISPOT.

FIG. 4: Adjuvant effect of Poly ICLC on IFN-gamma response of swine to PRRS virus in 6 week old pigs; see Example 4. Kinetics and intensity of the PRRSV-specific CMI response following immunization with MLV+poly ICLC as adjuvant. Pigs (n=6) were given a secondary immunization at week 9. CMI is expressed as group mean +/− SEM. *Denotes that the value is significantly different from vaccine only group (*$p<0.05$; **$p<0.07$).

DETAILED DESCRIPTION OF THE INVENTION

The following abbreviations are used herein:

complementary DNA: cDNA

Interferon α: IFNalpha or IFNα

Interferon β: IFNbeta or IFNβ

Interferon γ: IFNgamma or IFNγ modified live virus: MLV polyriboinosinic acid and polyribocytidylic acid complex: polyIC polyinosinic: polycytidylic acid, poly-L-lysine and carboxymethylcellulose complex: poly ICLC porcine reproductive and respiratory syndrome: PRRS As used herein, the phrase "enhancing an immune response" refers to the strengthening of an existing immune response to a pathogen and/or the initiation of an immune response to a pathogen.

Those of ordinary skill in the art recognize that there are a variety method for assessing such enhancements, for example, humoral antibody measurements, cytokine measurements, assessing animal health or well-ness, clinical protection from disease, and measuring cell mediated changes in immunity.

As used herein, the term "interferon" generally refers to any of a member of the family of molecules, sometimes referred to as cytokines, that have interferon activity such as modulation of immune response. The term "interferon" includes polypeptides and fragments thereof which have interferon activity such as chimeric or mutant forms of interferon in which sequence modifications are introduced, for example, to enhance selected characteristics of the molecule, without substantially affecting the nature of the biological activity (see U.S. Pat. Nos. 5,582,824, 5,593,667, and 5,594,107 all of which are incorporated by reference to the extent not inconsistent herewith.)

As used herein, the terms "porcine reproductive and respiratory syndrome" or "PRRS" refers to the causative agent of a disease sometimes referred to as "mystery swine disease", "swine infertility and respiratory syndrome", and "blue ear disease." The terms "porcine reproductive and respiratory syndrome" or "PRRS" are intended to include antigenic, genetic and pathogenic variations among PRRS virus isolates (Wensvoort et al., 1992, J. Vet. Diagn. Invest., 4:134-138; Mardassi et al., 1994, J. Gen. Virol., 75:681-685.)

As used herein a "vaccine composition" or "vaccine antigen composition" is any composition containing a molecule capable of stimulating an immune system response. This invention is particularly related to vaccines that stimulate an immune system response to a virus, and more specifically to a virus that is associated with a disease state of an animal. Vaccines for PRRS are of particular interest. The compositions and methods of this invention particularly relate to vaccine compositions that comprise modified live virus (MLV) and in this regard are particularly directed to vaccines that comprise an MLV of PRRS. Vaccine compositions may contain other ingredients as known in the art to facilitate or benefit functionality. Vaccine dosage levels for a given application can be determined by well-known methods.

As used herein an "adjuvant" is a molecule capable of enhancing an immune system response to a vaccine. In this invention an adjuvant composition can comprise a nucleic acid capable of expressing an interferon, particularly an interferon α. Interferon generated by expression from the exogenously administered nucleic acid sequence functions, alone or in combination with interferon generated by expression from endogenous nucleic acid sequences native to an animal, to enhance immune response to a vaccine that is administered to the animal. Interferon can directly or indirectly facilitate immune enhancement; for example, the interferon expressed from exogenously administered nucleic acid can induce or activate one or more intermediate species which in turn facilitates immune enhancement. In this invention an adjuvant composition can alternatively comprise a material that induces or enhances the activity of interferon, particularly interferon α. This material can function to induce or enhance the activity of interferon generated from exogenously administered expressible nucleic acid or that generated from endogenous nucleic acids native to the animal. The material can function directly to induce or enhance interferon activity or indirectly by induction or enhancement of the activity or expression of an intermediate species. The material may function to induce or enhance expression levels of an interferon or may otherwise enhance or activate interferon for enhancement of immune response. The material is present in the adjuvant composition at a level sufficient to enhance an immune response to a vaccine administered to an animal. Enhancement of immune response by an adjuvant of this invention is measured as any statistically significant increase in immune response compared to control response in the absence of the adjuvant as evaluated by any method accepted in the art. Adjuvant compositions may contain other ingredients as known in the art to facilitate delivery of an expressible nucleic acid to a cell or tissue for expression or facilitate delivery of the interferon inducer or enhancer to an appropriate cell or tissue. Dosage levels of adjuvant can be determined by well-known methods.

An adjuvant composition of this invention can comprise both a nucleic acid capable of expressing an interferon as well as a material that can induce or enhance activity of interferon. In this case the combined amounts of nucleic acid and the interferon inducer or enhancer are sufficient to result in a measurable enhancement of immune response to a given vaccine.

Preferred adjuvant compositions of this invention are those that comprise an expressible nucleic acid encoding an interferon α, a material which induces or enhances the activity of interferon α or both. Preferred materials which induce or enhance activity of interferon α include poly IC and poly ICLC.

Subunit Polypeptide Vaccines

The present invention also provides for vaccines comprising one or more PRRS virus or arterivirus polypeptides. A nucleic acid encoding such a polypeptide or polypeptides is constructed in a vector suitable for a prokaryotic or eukaryotic host and capable of expressing one or more PRRS virus polypeptides. Examples of such subunit/polypeptide PRRS vaccines are given in U.S. Pat. No. 6,251,397 to Paul et al. which is hereby incorporated by reference to the extent not inconsistent herewith. There are numerous *Escherichia coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the coding sequence. Also, the carboxy-terminal extension of the sequence can be removed using standard oligonucleotide mutagenesis procedures.

Alternative vectors for the expression of PRRS virus polypeptides in eukaryotic hosts, e.g., mammalian or porcine cells, similar to those developed for the expression of human gamma-interferon, tissue plasminogen activator, clotting Factor VIII, hepatitis B virus surface antigen, protease Nexinl, and eosinophil major basic protein, can be employed. Further, the vector can include cytomegalovirus promoter sequences and a polyadenylation signal available for expression of inserted DNAs in eukaryotic cells.

Vaccine Composition and Carriers

Compositions can be administered alone or in combinations, e.g., as a complex with cationic liposomes, encapsulated in anionic liposomes, enclosed in chochleates, or they can be encapsulated in microcapsules. Compositions can include various amounts of the selected composition in combination with a pharmaceutically acceptable carrier and, in addition, if desired, may include other medicinal agents, pharmaceutical agents, carriers, adjuvants, diluents, etc.

Any vaccine composition of this invention can comprise a pharmaceutically acceptable carrier. The pharmaceutically acceptable carrier in the vaccine of the instant invention can comprise saline or other suitable carriers (Arnon, R. (Ed.) Synthetic Vaccines 1:83-92, CRC Press, Inc., Boca Raton, Fla., 1987). An additional adjuvant can also be a part of the carrier of the vaccine, in which case it can be selected by standard criteria based on the antigen used, the mode of administration and the subject (Arnon, R. (Ed.), 1987). The DNA vaccines can be incorporated in liposomes or chocleates to enhance in vivo transfection. Genetic adjuvants, such as immunostimulatory sequences (ISS) and cytokine-encoding nucleic acids, can also be employed. See Horner A A et al., 1998, Immunostimulatory DNA Is a Potent Mucosal Adjuvant, Cellular Immunology 190:77-82, and Roman M et al., supra.

Additional Adjuvants

The compositions and methods of the invention can be administered with an additional adjuvant. In general, one or more than one additional adjuvant can be used to enhance the activity of the invention as long as a composition enhances the immune response to a vaccine or at least does not substantially inhibit the immune response. Examples of such adjuvants are found in "Vaccine design: the subunit and adjuvant approach" eds. Michael F. Powell and Mark J. Newman Pharmaceutical Biotechnology v. 6, Plenum Press 1995, New York, see e.g., chapter 7 "A compendium of Vaccine Adjuvants and Excipients" by Frederick R. Vogel and Micheal F. Powell and chapter 29, "cytokine-containing liposomes as adjuvants for subunit vaccines" by Lachman et al., which is hereby incorporated by reference. Examples of additional adjuvants that can be used in the invention include, but are not limited to, cytokines e.g., IL-2, IL-12, and other cytokines, cytokine-containing liposomes, alum (aluminum hydroxide), aluminum phosphate, and calcium phosphate.

Routes and Methods of Administration

Commercially available PRRS MLV currently indicates that administration of the vaccine should be performed parenterally by intramuscular injection using a conventional needle and syringe. However, embodiments of the present invention are not necessarily restricted to such route or method.

Vaccine compositions, including interferon-alpha and other materials like those that are inducers of interferon can be administered to a subject by any of many standard means for administering the particular composition. For example, compositions can be administered orally, sublingually, intraocularly, intranasally, intravenously, by intramuscular injection, intradermally, by intraperitoneal injection, topically, transdermally, and the like. Parental administration, if used, is generally characterized by injection. Injectables can be prepared in conventional forms, either as liquid solutions or suspensions, solid forms suitable for solution or suspension in liquid prior to injection, or as emulsions.

Other methods for delivery can include formulation with cationic lipids and liposomes; this can be applicable to either the DNA form or protein form of a cytokine adjuvant or to a chemical such as one capable of immune stimulation, for example by induction of an endogenous cytokine. See Pachuk C J et al., 2000, Curr Opin Mol Ther Apr 2(2): 188-98; Van Slooten M L et al. 2001, Biochim Biophys Acta 1530:134-45; Van Slooten M L et al., 2000, Pharm Res 17:42-48; Lachman L B et al., 1996, Eur Cytokine Netw 7:693-8. Further methods for delivery can include electroporation, cationic microparticles, ultrasonic distribution, and biolistic particle delivery techniques.

An embodiment of the invention comprises a mammalian expression vector containing porcine IFN-α cDNA. A particular embodiment comprises cDNA encoding porcine IFN-α was prepared by RT-PCR using RNA isolated from pig lymphocytes previously infected with pseudorabies virus (to stimulate IFN-α production). Primers were designed based on the nucleotide sequence of porcine IFN-α cDNA (Lefevre and La Bonnardiere 1986). Products of the anticipated size (590 bp) were cloned into the pCR®2.1 plasmid (Invitrogen Corp., Rockville, Md.), and an insert having the predicted restriction enzyme sites was sequenced. A comparison of the amplified sequence to the one previously reported revealed three nucleotide differences within the coding sequence. These differences resulted in two amino acid changes. The IFN-α cDNA was excised from the recombinant pCR®2.1 plasmid and placed under the transcriptional regulation of the cytomegalovirus promoter in pcDNA3 (Invitrogen Corp) to generate pINA3. To verify that an active cytokine was encoded by the amplified cDNA, Chinese hamster ovary (CHO) cells were transfected with pINA3 and single cell clones resistant to genticin were prepared. Supernatants from the clones were tested for the ability to inhibit the replication of an interferon-inducer negative strain of vesicular stomatitis virus in Madin Derby bovine kidney (MDBK) cells. Clones producing from 0 to greater than 200,000 units (1 unit inhibits 50% of VSV replication) of IFN-α were detected.

Another embodiment comprises a preparation of a chemical compound, polyICLC. In another particular embodiment, the following chemicals are obtained from Sigma-Aldrich (St. Louis, Mo.): Poly-L-Lysine (Cat. No. P0879), poly IC (Cat. No. P0913), and carboxymethylcellulose, low viscosity (Cat. No. C5678). Poly IC (500 ml; 4.0 mg/ml); poly-L-lysine (250 ml; 6.0 mg/ml); and 2% carboxymethylcellulose (250 ml) were prepared in pyrogen-free 0.85% NaCl. Poly ICLC (stabilized polynucleotide) was prepared following the method of Levy, Baer et al. (1975) with minor modifications. Poly I:C was re-annealed by heating at 71° C. for 1 hour and cooled slowly. Annealed poly I:C was then mixed with equal volumes of 6.0 mg/ml poly-L-lysine in normal saline and 2% carboxymethylcellulose. The final concentration of poly I:C was 1 mg/ml. This preparation was stored at 4° C. until needed.

THE EXAMPLES

Example 1

Challenge Study of PRRS MLV Vaccine Comprising IFNα cDNA Adjuvant

Enhanced immunity is achieved by supplementing a vaccine with a cDNA molecule capable of expressing interferon α. In an embodiment of the invention, Ingelvac® PRRS MLV is used with cDNA encoding porcine IFNα and capable of expressing IFNα. The Ingelvac PRRS MLV corresponds approximately to ATCC-VR2495, supra. The reproductive efficacy of PRRS MLV with porcine IFNα cDNA is measured relative to that of PRRS MLV alone via a clinical study. The key parameter of efficacy measured in the study is the number of piglets surviving through 28 days post-farrowing which were born to vaccinated female pigs, gilts, or sows as compared to the results for unvaccinated animals following PRRS virus challenge of both vaccinated and unvaccinated animals at about 90 days of gestation.

In a preferred embodiment of the invention, the cDNA encoding porcine IFNα is prepared as follows:

A cDNA copy of porcine interferon-α mRNA was prepared by the use of a reverse transcription-polymerase chain reaction (RT-PCR) in the following manner. Forward (INF-AF; SEQ ID NO:1 TCTGCAAGGTTCCCAATG) and reverse (INF-AR; SEQ ID NO:2 GTCTGTCACTCCTTCT-TCCTG) primers were designed based on the sequence of the porcine interferon-α gene presented in GenBank accession number X57191. The INF-AF primer is identical to the initiation codon of the porcine interferon-α transcript and the fifteen, upstream nucleotides whereas the complement of the translation termination signal and flanking sequences resides within primer INF-AR. The reverse primer was used to direct synthesis of cDNA by Superscript II reverse transcriptase (Life Technologies, Grand Island, N.Y.) from total RNA, isolated from pig leukocytes previously infected in vitro with pseudorabies virus (to stimulate production of interferon-α). The resulting products were amplified using the High Fidelity PCR System (Boehringer-Mannheim, Indianapolis, Ind.) and both INF-AF and INF-AR primers. An amplicon of the predicted size (590 bp) was purified by agarose gel electrophoresis and subsequently cloned into the TA vector, pCRII (Invitrogen, Carlsbad, Calif.), to create pSIN3.

Initial indication that pSIN3 contained the porcine interferon-α cDNA was based on the demonstrated presence of predicted restriction endonuclease sites within the insert. A comparison of the nucleotide sequence of the cloned amplicon (FIG. 1) to that described in the GenBank submission showed 99% identity with only three mismatches. These were a G to C, A to G, and G to T change at positions 327, 341, and 437, respectively. The nucleotides and amino acids that are divergent from those of sequence in GenBank: X57191 are in bold.

Figure 1:
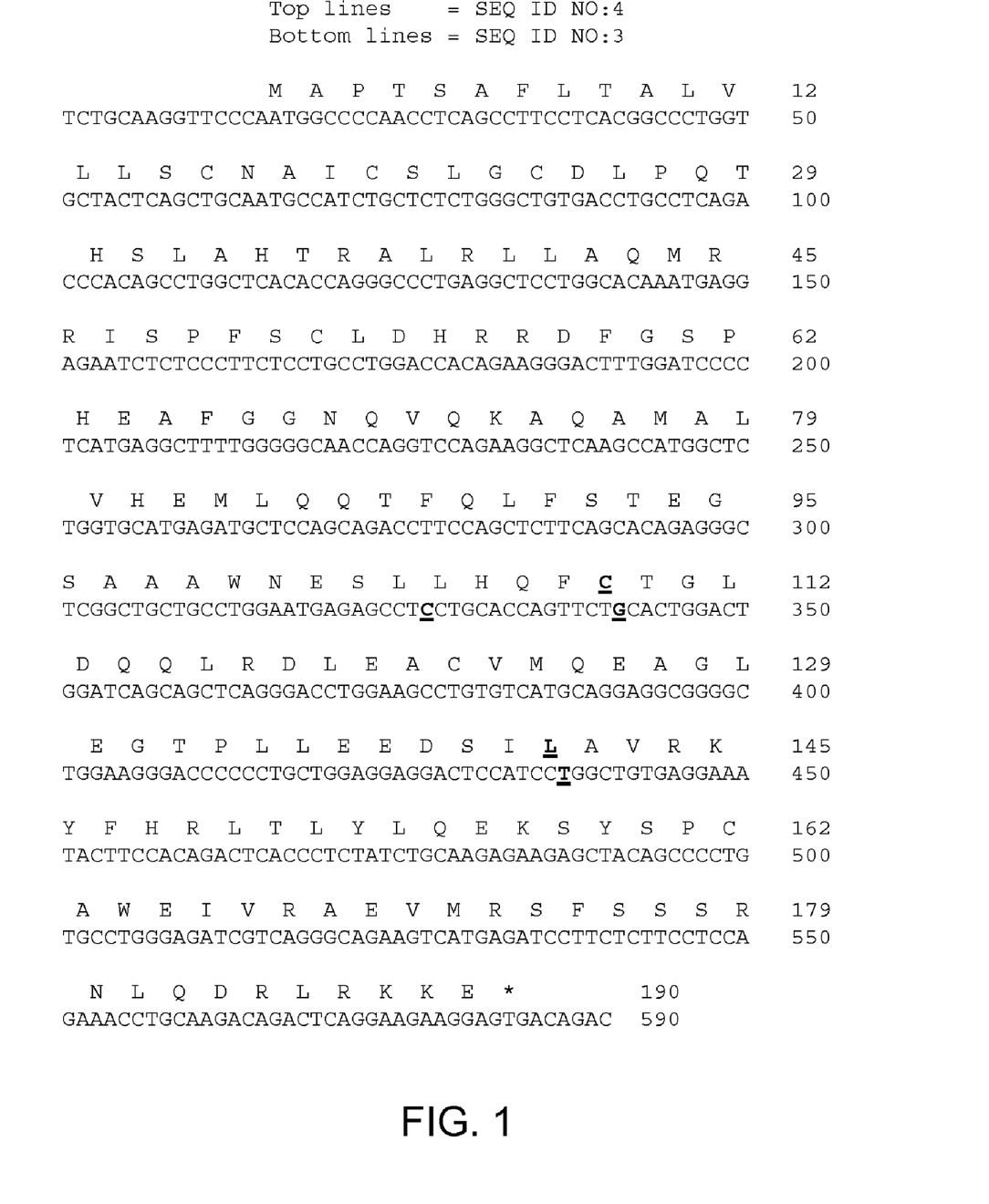

These different nucleotides resulted in no change in primary structure: a non-conservative replacement of tyrosine by cysteine, and a non-conservative replacement of arginine by leucine, respectively (FIG. 1). Whether these alterations are due to amplification errors, polymorphisms in the interferon-α gene, or to amplification of a transcript arising from a non-allelic interferon-α gene (there are at least eleven) is unclear.

Figure 2:
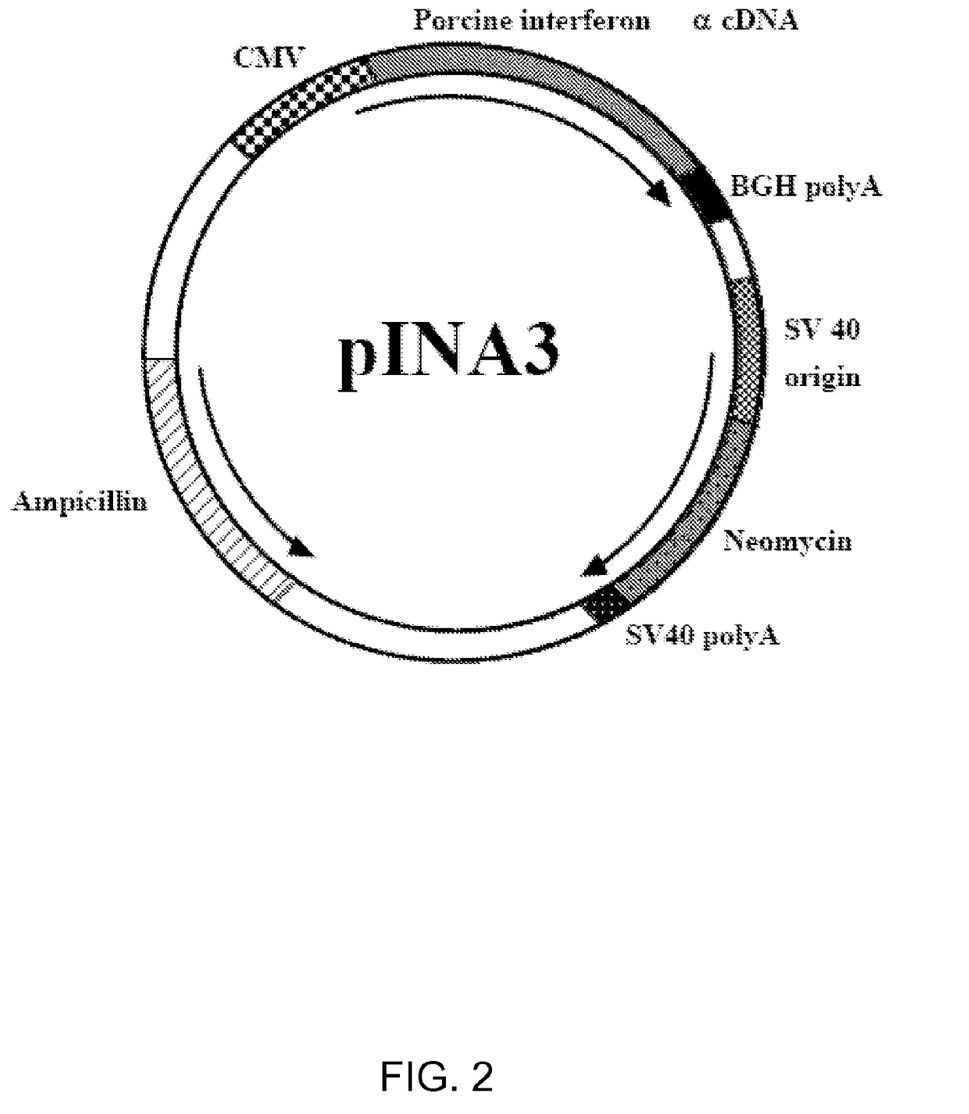
Figure 3:
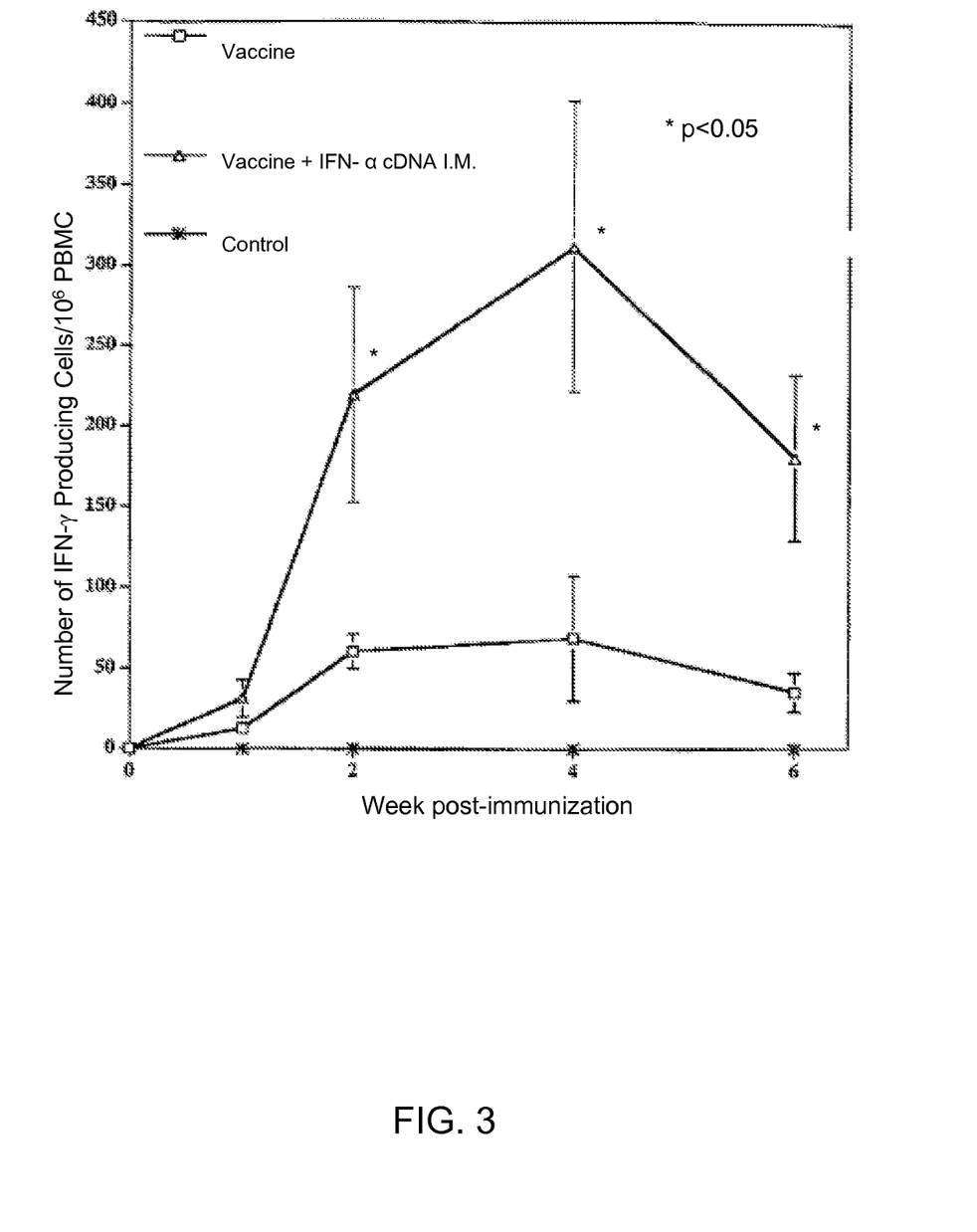

To determine whether the amplified porcine interferon-α cDNA encoded an authentic cytokine, the intact cDNA was excised from pSIN3 by digestion of the plasmid with Hind III and Xho I and inserted into the respective sites of the eucaryotic expression vector pcDNA3 (Invitrogen) to create pINA3 (FIG. 2). In FIG. 2, the relative positions and direction of transcription of the cytomegalovirus promoter (CMV) porcine interferon alpha cDNA, bovine growth hormone polyadenylation signal sequence (BGH polyA), SV40 origin of replication, bacterial neomycin resistance gene, SV40 polyadenylation signal sequence (SV40 polyA) and bacterial ampicillin resistance gene are indicated.

In this plasmid, expression of the inserted porcine interferon-α cDNA is regulated by the cytomegalovirus enhancer-promoter and the resulting transcripts are polyadenylated due to a downstream bovine growth hormone polyadenylation signal sequence. Chinese hamster ovary (CHO) cells were then transfected with pINA3 and 48 hr later the overlaying medium was assayed for the presence of porcine interferon-α in the following ways. First, the ability to inhibit vesicular stomatitis virus (VSV) replication in Madin-Darby bovine kidney (MDBK) cell monolayers was examined. Second, the ability to stimulate porcine leukocytes to produce interferon-γ was tested. Since positive results were obtained only when using the supernatants from pINA3-transfected cells, production of a biologically active cytokine was evident.

The PRRS vaccine comprises any effectively attenuated form of PRRS. A particular example is a serial or lot of Ingelvac PRRS® MLV manufactured according to the commercial outline of production and used per label directions. The experimental material is a similar PRRS vaccine to which a quantity of nucleic acid vector containing expressible cDNA for porcine IFNα is added, in a range of 0.1 to 1000 µg per kg of body weight. Alternatively, the experimental material is the PRRS vaccine and the quantity of IFNα nucleic acid which are not mixed together but delivered to the test subject separately.

In a preferred embodiment, the test subjects are a commercial cross breed of female porcine animals of an age used in breeding operations. The gilts or sows are about at least 6 months of age and of approximately uniform weight for age. The animals are confirmed as having naive serological status with respect to PRRS as measured by IDEXX PRRS ELISA (Westbrook, Me.), a commercially available test for porcine antibody specific to PRRS antigens. The gilts or sows are vaccinated with a composition of the invention from about 4 weeks prior to 1 week prior to breeding, with or without previous vaccination, and the animals are not exposed to either the vaccine composition or the interferon alpha adjuvant component during gestation.

In another embodiment, the test subjects are pigs about at least 3 weeks of age at the time of vaccination and may or may not receive a second vaccination prior to breeding.

In yet another embodiment, the females are confirmed as pregnant by ultrasound and are vaccinated with a composition of the invention at from about 30 days to about 45 days of gestation at the time of vaccination.

In a particular embodiment, the clinical study includes four test groups of 8 female breeding animals per group. Group 1 receives PRRS MLV on Day 0, equivalent to about 30 days of gestation. Group 2 receives PRRS MLV supplemented with cDNA for porcine IFNα. The inoculation of animals with challenge virus occurs on about Day 60, the equivalent of about 87 to 92 days of gestation. Group 3 animals are not vaccinated but are challenged. Alternatively, Group 3 animals are treated with the inverted coding sequence of IFNalpha as a control and then challenged. Group 4 animals are not vaccinated and not challenged. The farrowing performance is evaluated by observing the health status of the piglets born.

The challenge material is a virulent strain of PRRS virus, strain 17198-6. The challenge material is diluted in Modified Eagles Medium supplemented with 4% fetal calf serum such that the concentration is about log10 3.5+/−0.5 per ml. The challenge dose is administered by giving a total of 2 ml intranasally, one ml per nostril. The intranasal administration is performed using 2 ml of challenge material and a syringe with 16 gauge catheter tubing. The challenge strain can be derived from any virulent PRRS virus such as a field isolate. Another example of another suitable challenge strain is ATCC VR-2385 (Thanawongnuwech, R. et al. 1997 Vet. Immunol. Immunopathol. 59:323-335.)

Following challenge, multiple analyses are performed including evaluation of serological data, viremia data, body temperature data, clinical observations, and farrowing results. The transplacental transmission of PRRS virus after administration of the virus is evaluated. The farrowing performance of the sows is the main criterion used to determine efficacy of the test articles. Specifically, the number of mummies versus stillborn fetuses (autolyzed in utero death versus fresh-dead) are compared, and parameters including the health status and performance of the pigs born alive through 28 days post farrowing are monitored.

The results between and among groups are compared to determine the degree of immune enhancement achieved by immunization with PRRS MLV alone versus immunization using PRRS MLV and cDNA for porcine IFNα.

In another embodiment, one or more than one vaccination (administration) of PRRS MLV is given in conjunction with one or more than one administration of cDNA for porcine IFNα where the vaccination and administration can occur at the same or different times. The administrations of vaccine and adjuvant, if separate, are preferably contemporaneous, i.e., administered within a time span that is sufficiently short that the immune enhancement can occur, preferably within about one week of vaccination. Substantially simultaneous administration (separate administrations of vaccine and adjuvant) with rapid sequential administration or co-administration of the vaccine and adjuvant can be employed. Alternatively, separate administration of vaccine and adjuvant can occur at intervals up to about one week.

Example 2

Adjuvant Effect of IFNalpha cDNA on IFNgamma Response to PRRS MLV

Eight-week-old Yorkshire×Landrace cross-bred pigs were obtained from an unvaccinated, specific-pathogen-free (SPF) facility at the University of Illinois Veterinary Research Farm. The pigs were randomly segregated into 3 groups. One group (n=5) of pigs was immunized intramuscularly (I.M.) into the adductor muscle (inner thigh) with 2.0 ml of PRRS MLV vaccine (Ingelvac PRRS MLV; Nobl). A second group of pigs (n=5) was vaccinated with the same MLV vaccine immediately followed by an intramuscular injection at an adjacent site of 200 µg of a plasmid containing the cDNAs for the porcine IFN-α. A third group (n=2 pigs) remained as unvaccinated negative controls that were maintained in a separate room. Peripheral blood mononuclear cells were isolated weekly and used to monitor the virus-specific immune response to the PRRS virus vaccine. The number of PRRS virus-specific IFN-gamma-secreting cells was measured using an ELISPOT assay (as described in Zuckerm gain within the first four weeks of age. Liveborn piglets that die during the study are weighed as soon as possible after death. Clinical observations include behavior, respiration, and cough per raw observations or a scoring system.

Following data collection, analyses are performed including evaluation of serological data, viremia data, body temperature data, clinical observations, performance data including weight gain, survival data, and farrowing results.

The results between and among groups are compared to determine the degree of immune enhancement achieved by immunization with PRRS MLV alone versus immunization using PRRS MLV and polyICLC.

In another preferred form of the invention, one or more than one vaccination of PRRS MLV is given in conjunction with one or more than one administration of polyICLC, where the vaccination and administration can occur at the same or different times. Preferably the intervals between administration of separate vaccine and adjuvant or multiple administrations of vaccine and adjuvant are less than about one week.

Example 4

Adjuvant Effect of Poly ICLC on IFNgamma Response of Swine to PRRS Virus

As an alternative to a challenge study, the enhancement effect of vaccine compositions is evaluated by measuring increased levels of IFNgamma post-vaccination. Twelve 6-week-old Yorkshire×Landrace cross-bred pigs were obtained and randomly assigned to 2 groups (n=6). The first group was immunized intramuscularly with 2.0 ml of PRRS MLV vaccine (Ingelvac PRRS MLV; Nobl). The other group was immunized with PRRS MLV vaccine co-administered with 0.25 mg/kg of poly ICLC. This dose of poly ICLC has been shown to induce maximum IFNα titers in the sera of 10-week-old pigs (see Lowen K. G. and Derbyshire, J. B. 1988. Interferon induction in piglets with polyinosinic:polycytidilic acid complexed with poly-L-lysine and carboxymethylcelulose. Research in Veterinary Science 44:132-133). Pigs in both groups were given a secondary "booster" immunization 8 weeks following primary immunization that included poly ICLC for the appropriate group. Peripheral blood mononuclear cells were isolated weekly and used to monitor the virus-specific immune response to the PRRS virus vaccine. The number of PRRS virus-specific IFN-gamma-secreting cells was measured using an ELISPOT assay as described (Zuckermann et al. 1998).

Figure 4:
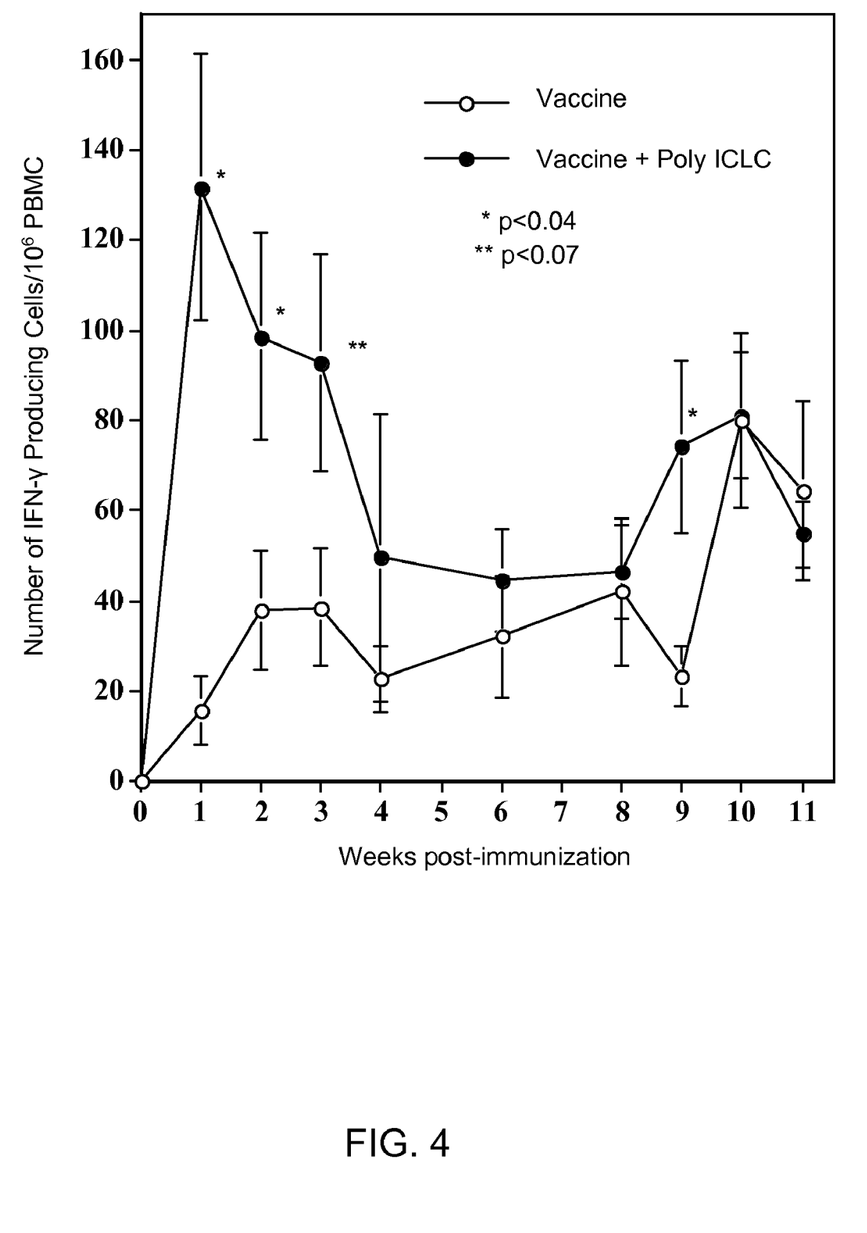

The accompanying figure (FIG. 4) shows the enhancing effect of polyICLC on the virus-specific IFN-gamma response to vaccination against PRRSV. Groups of pigs (n=5) were immunized with a commercial PRRSV modified live virus vaccine given either alone (open squares) or in combination with the simultaneous intramuscular injection at an adjacent site of polyICLC at a dose of 0.25 mg/kg of body weight (open diamonds). At the indicated times peripheral blood mononuclear cells were isolated from these animals and tested in an IFN-gamma ELISPOT assay as described (Zuckermann et al., 1998). The IFN-gamma response is expressed as the group mean frequency of virus-specific IFN-g-secreting cells/$10^6$ PBMC±standard error of the mean.

Example 5

Studies of an Inactivated, Subunit, or Attenuated PRRS Vaccine Comprising IFNα cDNA Adjuvant In this example, circumstances are similar to that for the examples with the PRRS MLV vaccine (with or without challenge), but the PRRS vaccine here comprises either an inactivated form of PRRS or comprises a subunit of PRRS, such as a polypeptide. Alternatively, the PRRS vaccine comprises an attenuated form of PRRS that is attenuated by a process other than that corresponding to the process for the PRRS MLV specifically described as the Ingelvac type. The process of attenuation can be achieved by methods known in the art such as passage in vitro, passage in foreign hosts, or by methods including genetic engineering. A non-limiting example of such an attenuated strain can be derived from ATCC VR-2385.

Any examples provided are not intended as exclusive or limiting; the scope of the claims is intended to be determined by the claim language and not by specific examples or embodiments listed. All references cited herein are incorporated in their entirety by reference herein to the extent that they are not inconsistent with the disclosure herein.

What is claimed:

1. A purified nucleic acid composition comprising SEQ ID NO:3.

\* \* \* \* \*

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 1
tctgcaaggt tcccaatg                                                  18

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer -continued

```
<400> SEQUENCE: 2
gtctgtcact ccttcttcct g                                              21

<210> SEQ ID NO 3
<211> LENGTH: 590
<212> TYPE: DNA
<213> ORGANISM: Porcine
<220> FEATURE:
<221> NAME/KEY: CDS
<222> LOCATION: (16)..(582)

<400> SEQUENCE: 3
tctgcaaggt tccca atg gcc cca acc tca gcc ttc ctc acg gcc ctg gtg    51
                 Met Ala Pro Thr Ser Ala Phe Leu Thr Ala Leu Val
                  1               5                  10 cta ctc agc tgc aat gcc atc tgc tct ctg ggc tgt gac ctg cct cag    99
Leu Leu Ser Cys Asn Ala Ile Cys Ser Leu Gly Cys Asp Leu Pro Gln
             15                  20                  25 acc cac agc ctg gct cac acc agg gcc ctg agg ctc ctg gca caa atg   147
Thr His Ser Leu Ala His Thr Arg Ala Leu Arg Leu Leu Ala Gln Met
         30                  35                  40 agg aga atc tct ccc ttc tcc tgc ctg gac cac aga agg gac ttt gga   195
Arg Arg Ile Ser Pro Phe Ser Cys Leu Asp His Arg Arg Asp Phe Gly
 45                  50                  55                  60 tcc cct cat gag gct ttt ggg ggc aac cag gtc cag aag gct caa gcc   243
Ser Pro His Glu Ala Phe Gly Gly Asn Gln Val Gln Lys Ala Gln Ala
                 65                  70                  75 atg gct ctg gtg cat gag atg ctc cag cag acc ttc cag ctc ttc agc   291
Met Ala Leu Val His Glu Met Leu Gln Gln Thr Phe Gln Leu Phe Ser
             80                  85                  90 aca gag ggc tcg gct gct gcc tgg aat gag agc ctc ctg cac cag ttc   339
Thr Glu Gly Ser Ala Ala Ala Trp Asn Glu Ser Leu Leu His Gln Phe
         95                 100                 105 tgc act gga ctg gat cag cag ctc agg gac ctg gaa gcc tgt gtc atg   387
Cys Thr Gly Leu Asp Gln Gln Leu Arg Asp Leu Glu Ala Cys Val Met
    110                 115                 120 cag gag gcg ggg ctg gaa ggg acc ccc ctg ctg gag gag gac tcc atc   435
Gln Glu Ala Gly Leu Glu Gly Thr Pro Leu Leu Glu Glu Asp Ser Ile
125                 130                 135                 140 ctg gct gtg agg aaa tac ttc cac aga ctc acc ctc tat ctg caa gag   483
Leu Ala Val Arg Lys Tyr Phe His Arg Leu Thr Leu Tyr Leu Gln Glu
                145                 150                 155 aag agc tac agc ccc tgt gcc tgg gag atc gtc agg gca gaa gtc atg   531
Lys Ser Tyr Ser Pro Cys Ala Trp Glu Ile Val Arg Ala Glu Val Met
            160                 165                 170 aga tcc ttc tct tcc tcc aga aac ctg caa gac aga ctc agg aag aag   579
Arg Ser Phe Ser Ser Ser Arg Asn Leu Gln Asp Arg Leu Arg Lys Lys
        175                 180                 185 gag tgacagac                                                        590
Glu

<210> SEQ ID NO 4
<211> LENGTH: 189
<212> TYPE: PRT
<213> ORGANISM: Porcine

<400> SEQUENCE: 4

Met Ala Pro Thr Ser Ala Phe Leu Thr Ala Leu Val Leu Leu Ser Cys
  1               5                  10                  15
```

-continued

```
Asn Ala Ile Cys Ser Leu Gly Cys Asp Leu Pro Gln Thr His Ser Leu
             20                  25                  30

Ala His Thr Arg Ala Leu Arg Leu Leu Ala Gln Met Arg Arg Ile Ser
             35                  40                  45

Pro Phe Ser Cys Leu Asp His Arg Arg Asp Phe Gly Ser Pro His Glu
     50                  55                  60

Ala Phe Gly Gly Asn Gln Val Gln Lys Ala Gln Ala Met Ala Leu Val
 65                  70                  75                  80

His Glu Met Leu Gln Gln Thr Phe Gln Leu Phe Ser Thr Glu Gly Ser
             85                  90                  95

Ala Ala Ala Trp Asn Glu Ser Leu Leu His Gln Phe Cys Thr Gly Leu
            100                 105                 110

Asp Gln Gln Leu Arg Asp Leu Glu Ala Cys Val Met Gln Glu Ala Gly
            115                 120                 125

Leu Glu Gly Thr Pro Leu Leu Glu Glu Asp Ser Ile Leu Ala Val Arg
    130                 135                 140

Lys Tyr Phe His Arg Leu Thr Leu Tyr Leu Gln Glu Lys Ser Tyr Ser
145                 150                 155                 160

Pro Cys Ala Trp Glu Ile Val Arg Ala Glu Val Met Arg Ser Phe Ser
            165                 170                 175

Ser Ser Arg Asn Leu Gln Asp Arg Leu Arg Lys Lys Glu
            180                 185
```